United States Patent [19]

Anderson et al.

[11] 4,314,412
[45] Feb. 9, 1982

[54] ORTHOPEDIC SHOE

[76] Inventors: Blair V. Anderson, 1695 Lakeside Dr., Reno, Nev. 89509; Morris Feldman, 528 "B" St., Santa Rosa, Calif. 95401; Richard Jacoby, 12439 N. 32nd St., Phoenix, Ariz. 85032

[21] Appl. No.: 132,258

[22] Filed: Mar. 20, 1980

[51] Int. Cl.³ .......................... A43B 3/24; A43B 3/14; A43B 13/08
[52] U.S. Cl. ...................... 36/100; 36/11.5; 36/33
[58] Field of Search ................... 36/100, 101, 11.5, 13, 36/85, 93, 95

[56] References Cited

U.S. PATENT DOCUMENTS

| | | | |
|---|---|---|---|
| 1,486,630 | 3/1924 | Burnett | 36/11.5 |
| 2,370,301 | 2/1945 | Ghez et al. | 36/33 |
| 2,415,459 | 2/1947 | Buselmeier | 36/11.5 |
| 3,455,037 | 7/1969 | Vlas et al. | 36/11.5 |
| 4,124,946 | 11/1978 | Tomlin | 36/11.5 |
| 4,188,735 | 2/1980 | Hahn | 36/11.5 |
| 4,200,997 | 5/1980 | Scheinhacs et al. | 36/11.5 |

*Primary Examiner*—Patrick D. Lawson
*Attorney, Agent, or Firm*—Herbert C. Schulze

[57] ABSTRACT

This invention is an orthopedic shoe particularly characterized by special configuration, both on the portion of the shoe which is in contact with the foot and the portion which is in contact with the surface to be walked upon. It is particularly characterized by special openings with various types of removable closures to the openings to accommodate unusual problems and by removable build-up layers for foot contact. It is further characterized by rigidity and a "rocker" configuration with a fully adjustable and removable upper fastening member.

6 Claims, 15 Drawing Figures

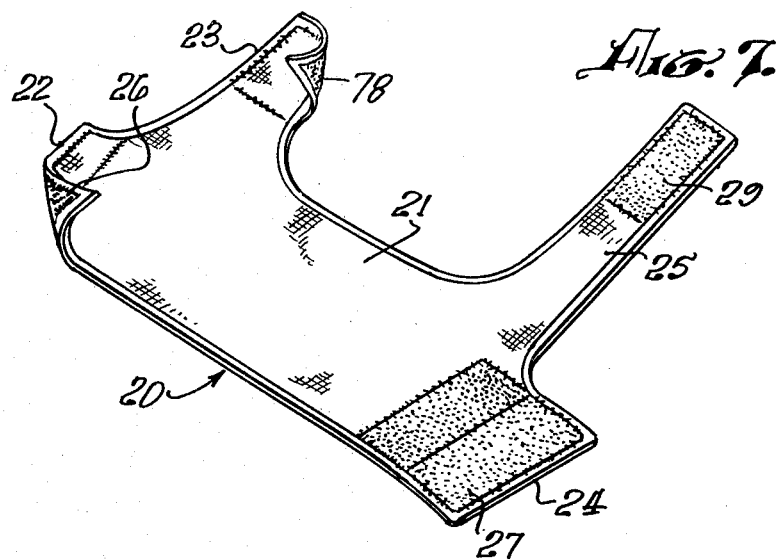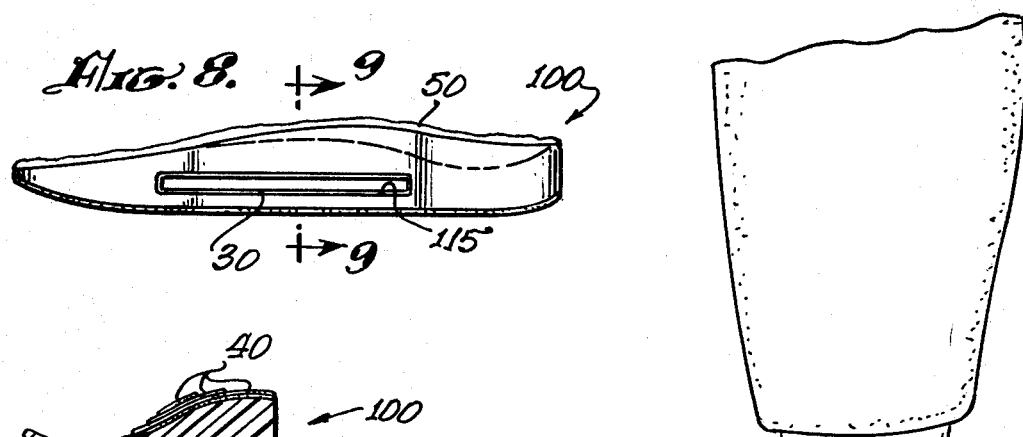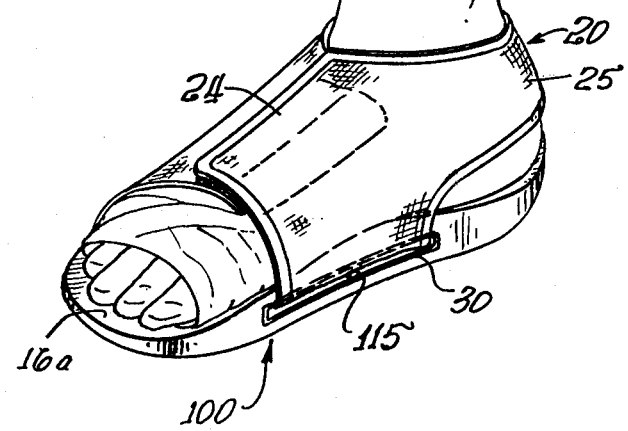

ORTHOPEDIC SHOE

BACKGROUND OF THE INVENTION

1. Field of the Invention

This invention is in the general field of orthopedic shoes, and is more particularly in the field of an orthopedic shoe designed specifically to provide appropriate, yet comfortable, support for those with foot problems and/or those wearing leg casts, or the like. The invention is even more particularly directed to such a shoe which can be used not only for orthopedic purposes, but actually can likewise be used for a variety of other ordinary purposes where economical shoes are desired which include ease of use, universal sizing, and cleanliness.

2. Description of the Prior Art

There has been much work and there have been many variations of orthopedic shoes and other shoes for essentially all of the period of civilization. Many shoes have special configurations on the soles and many shoes have special configurations on their interiors to support the arch and the like. Also, it is known to make shoes having a rigid sole for use in cases where casts are applied to injured legs or ankles and to attempt to recite every conceivable shoe which has ever been designed would be impossible.

We know, however, that the present shoe is unique in providing the first thoroughly rigid shoe adaptable to almost all foot sizes and shapes with a fastening strap incorporated therein which provides for immediate fastening over bandages, casts, or the like as necessary with removable inserts at various positions to accommodate unusual foot problems. Thus we consider the present invention to be unique as compared to any past art.

THE SUMMARY OF THE INVENTION

The human foot is one of the most critical parts of the entire human anatomy. Frequently various ailments can be traced to foot problems, and most people are dependent for good health upon proper and comfortable functioning of their feet and legs.

Unfortunately, there are many common foot ailments, and additionally, the foot, ankle, and leg are particularly vulnerable in accidents and are frequently fractured; at these times, special bandages, casts, and other aides must be applied to assist the healing process. Further, many persons will have bunions or other foot problems which are painful unless carefully supported and cared for.

We have studied this problem for a very long time and have ascertained a number of requirements which simply cannot be met by shoes and appliances which have been available in the past. In our study we determined that it must be possible to have a shoe which can be easily and economically custom fitted to the foot of the individual using it. Further, however, for many orthopedic uses said shoe must also be quite rigid and should be shaped in such manner that the user can essentially "rock" on it from heel to toe. Further, we have ascertained that for many conditions of casts or the like it is important to have the toe portion of the foot support sloping downward from the arch.

Additionally, we have determined that most shoes are incapable of proper use when one is using a foot cast.

To further complicate the matter, some persons must have special relief areas into which a bunion or other growth can protrude without being contacted so as to cause pain.

In studying the various requirements heretofore set forth, we further came upon the desirability of having a shoe for many general uses which shoe would in essence substitute for sandals and the like, and would be sanitary and adjustable over a wide range of foot conditions. We further ascertained that some of the same desirable characteristics of a strictly orthopedic shoe would be most desirable for a number of special activities such as gardening, beachwear, and the like.

With the foregoing in mind, we have now developed a shoe which comprises essentially a rigid platform having its underside essentially flat, over most of its length, but with a suitable curved front and rear portion so that a true "rocking" action can take place during walking.

We then provided a specially configured upper portion to the platform wherein a suitable arch configuration has been formed with a depressed heel portion and with a toe portion tapering gradually in a downwardly direction from the arch portion.

We next continued the process of studying the foot and determined that in the area of the ball of the foot, and in the toe area, there could be special problems. Also the same special problems exist for the heel area. We therefore provided removable plugs specially configured within these areas which can be taken out as desired to provide appropriate openings into which sensitive areas may protrude. We also discovered that we were able to provide not only the arch, but other areas of the shoe, with removable adhering strap elements to gradually build up any particular area for appropriate foot contact. This is particularly true in the arch area, but also can be true in other areas.

Lastly, we were faced with the dilemma of providing an appropriate upper for this shoe platform so that it could quickly and earily adjust to all varying conditions such as encompassing a cast, or fitting quickly on various foot sizes.

We accomplished this latter goal by providing a strap essentially in the shape of a "U" within and extending through the platform approximately in the arch area, wherein the straps can be closed over the top of the foot, and the two ends forming the "U" can wrap around the heel. By the use of Velcro fastening material this arrangement can accommodate a wide range of differing sizes with complete comfort.

In its most preferred structure, this "U" shaped element will slip through an aperture in such manner that it can be removed quickly and easily for washing, or for substituting varying colors if desired, or for applying bandages or the like, to a foot with no difficulty of removal of the foot from the shoe.

As previously mentioned, while originally the shoe was designed as a strictly orthopedic shoe, by some of the modifications we have made, we have transformed it into a shoe for many general purposes. For example, it is an excellent platform upon which to walk across wet or other uncomfortable surfaces. This is but one example of its many uses which are almost limitless.

It is an object of this invention to provide a shoe which can adapt to varying foot sizes.

Another object of this invention is to provide such as shoe as heretofore mentioned wherein it is composed of a rigid platform with a flexible and widely adjustable fastening for its upper.

Another object of this invention is to provide such a shoe as heretofore mentioned wherein special removable or adherable elements may be applied to accommodate unusual foot conditions.

Another object of this invention is to provide such a shoe as described wherein it can be used properly by those wearing a cast.

The foregoing and other objects and advantages of this invention will become clear to those skilled in the art upon reading the description of a preferred embodiment which follows in conjunction with a review of the appended drawings.

BRIEF DESCRIPTION OF THE DRAWINGS

FIG. 7 is a perspective view of the attachment means of FIG. 1, but removed from the shoe and opened out to a nearly flattened condition for clarity;

FIG. 8 is a first modified form of the preferred embodiment of FIG. 1, showing certain variations of construction;

FIG. 9 is an enlarged sectional view taken on line 9—9 of FIG. 8 to further illustrate these modifications;

FIG. 10 is a perspective view of a leg of a patient wearing a cast and utilizing the orthopedic shoe for walking;

DESCRIPTION OF A PREFERRED EMBODIMENT

Figure 1:
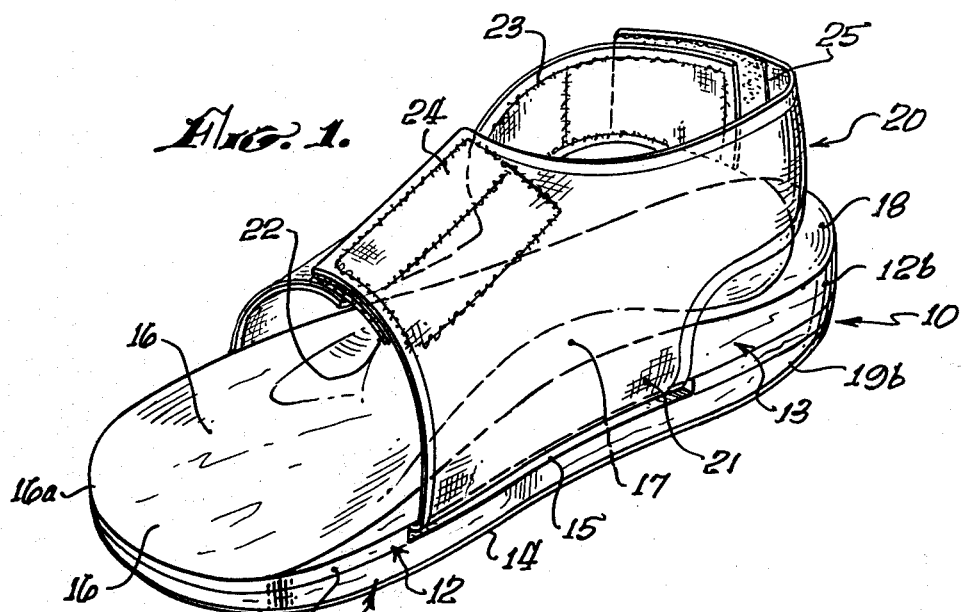
FIG. 1 is a perspective view of a preferred embodiment of a shoe or sandal of this invention.
Figure 2:
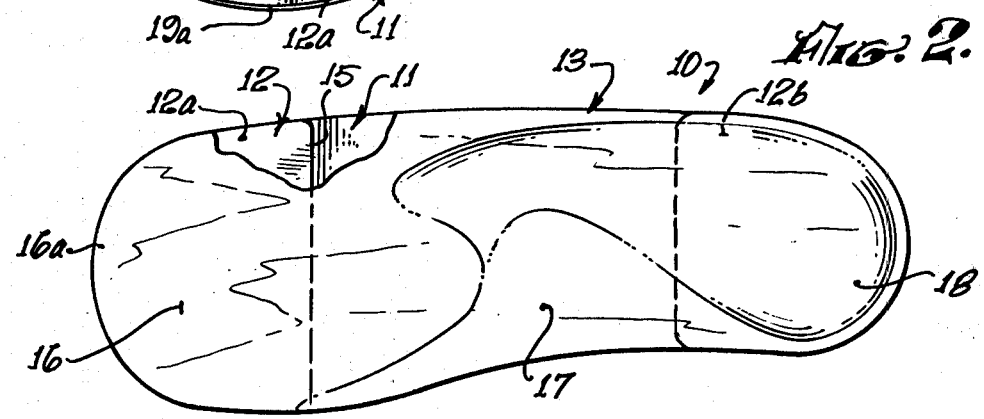
FIG. 2 is a top plan view of the device shown in FIG. 1 with the attachment means removed and the shoe shown partly broken away.
Figure 3:
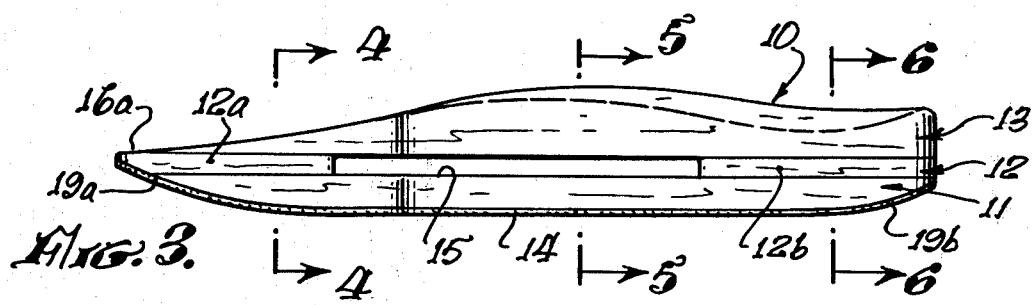
FIG. 3 is a side elevational view of FIG. 2.
Figures 4, 5, 6:
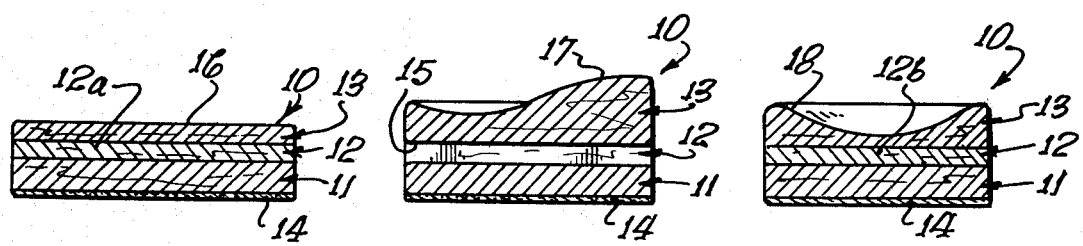
FIGS. 4, 5, and 6 are sectional views taken along lines 4—4, 5—5, and 6—6 of FIG. 3.
Figure 11:
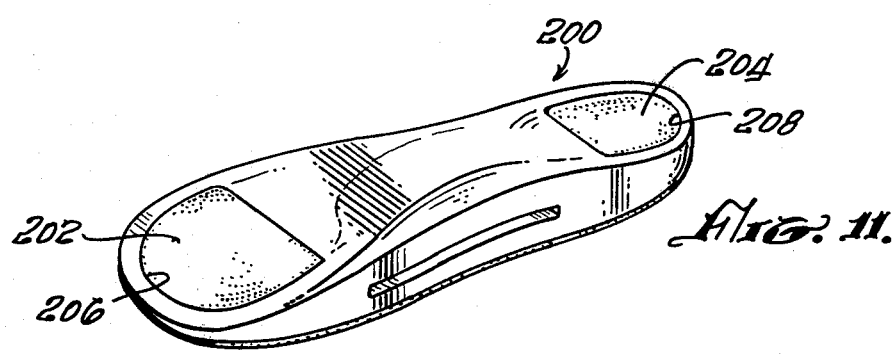
FIG. 11 is a second modified embodiment of the orthopedic shoe.
Figure 12:
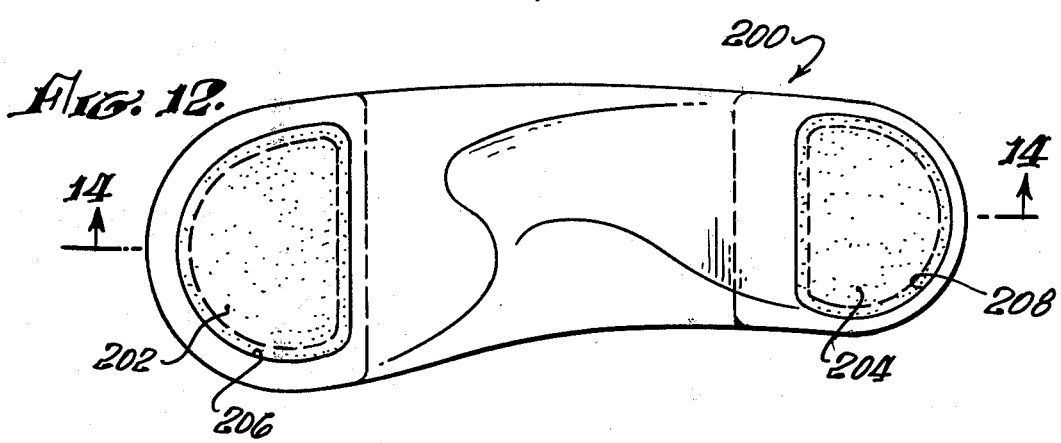
FIG. 12 is a top plan view of the shoe indicated in FIG. 11.

In FIG. 1 we have illustrated an orthopedic shoe designated by the reference numeral 10 and a means 20 of attaching to a foot of a user. The shoe is constructed of three strips of material such as wood, plastic or any durable material. In the form which is illustrated in FIGS. 1 through 6 we have bonded together three layers of said material, indicated by the reference numerals 11, 12, and 13. A bottom layer of material 14 may be added to complete the shoe and to provide a protective layer for longer wear and for non-slipping properties. The middle layer 12 is composed of two pieces 12a and 12b spaced apart in order to allow a slot 15 to be formed in the shoe. This slot permits the attachment means 20 to pass through in a manner to be described later in this application.

The topmost layer 13 is formed into a configuration having sole portion 16 arch portion 17, and heel portion 18. These various portions are contoured to accept the general shape of a foot as can be understood by those familiar in the art.

The bottom of the shoe can be shaped at its forward toe end into a curve 19a, while the heel end of the same bottom surface 19b is also curved as shown. This particular curving feature allows the shoe to be worn by a patient whose leg is heavily bandaged for treatment of an injury or ailment, or wearing a cast. While wearing this shoe, the patient can walk with a "rocking" action, thereby not having to move an injured ankle or to bend an injured knee.

The shoe can be contoured for a left foot or a right foot, or for a particular distortion on the foot such as a bandage or pad or a physical enlargement such as swelling.

The attachment means 20 shown in FIG. 7 in a flattened condition comprises a central portion 21 of a large area which will be inserted into the slot 15 by passing an extended end 22 and a perpendicular band 23 through the slot. After the patient has placed his foot onto the shoe, the end portion 22 of attachment means 20 is brought up about the foot and joins a second extending portion 24 of the band, thereby securing the foot against the top layer 13 of the shoe. The extending end 23 is then wrapped around the ankle and makes contact with a longer band 25. By means of Velcro pads 26, 27, 28, and 29, or the like, the shoe firmly adheres to the foot.

A first modified form of our orthopedic shoe is indicated in FIG. 8 and referred to by the reference numeral 100. This shoe can be molded from a suitable material into a one piece construction allowing a slot 115 to be formed therein. A metal sleeve 30 can be inserted and bonded within the slot in order to further strengthen the modified shoe. The contouring on the top surface of the shoe can be modified to whatever configuration suits the patient's needs and this modification can be done by applying any number of layers of material such as tape 40.

The cross-section of FIG. 9 shows a plurality of these tapes having been applied to change the initially formed contour of the shoe.

In FIG. 8, a layer of soft material 50 such as foam rubber or plastic can be added for the comfort of the patient.

FIG. 10 is a perspective showing the bandaged foot of a patient wearing a cast and utilizing a shoe of this invention. As can be seen in this Figure and the Figures preceeding, the downwardly tapering surface 16 can drop off to a point 16a allowing space for bandages and the like, without distorting the natural plane that the foot normally assumes in a standing condition.

In the modification shown in FIGS. 11 through 15, we have shown the shoe 200 as having cavities formed therein in order to allow for inserts to be placed at the toe and heel portions. The inserts 202 and 204 are placed into tapered cavities 206 and 208. These inserts may be formed of a resilient material such as rubber or plastic and can be molded into configurations that will suit the needs of a patient's foot.

Figure 15:
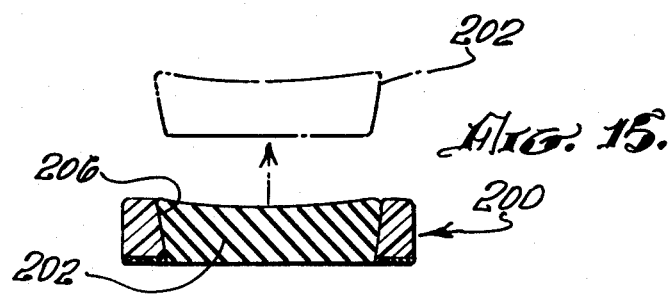
FIG. 15 is a sectional view taken on line 15—15 of FIG. 13.

As indicated in FIG. 15, one can easily push the insert up by pressure from the bottom of the shoe and another insert may be placed into the cavity for the use by another patient or the same patient having further changes in his foot configuration.

Figure 13:
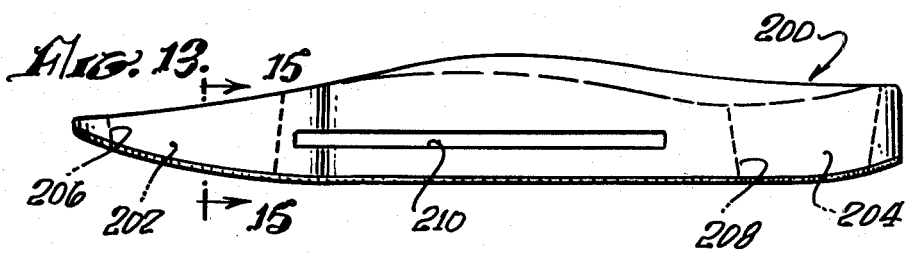
FIG. 13 is a side elevational view of the shoe in FIG. 12.
Figure 14:
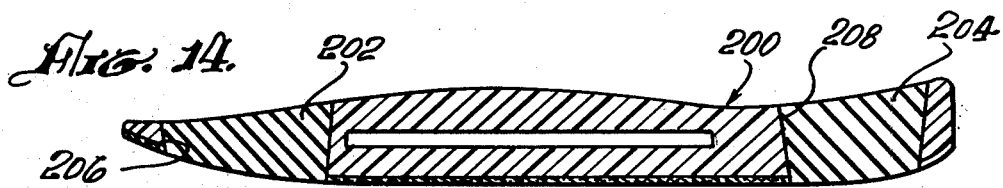
FIG. 14 is a longitudinal section taken on line 14—14 of FIG. 12.

A particular comment should be made that while the universally adaptable upper portion of this invention as illustrated has been shown in the drawings to be removable, and while this is considered far preferable for purposes of cleanliness and replacing with different colors and the like, it is understood that an apparatus such as is shown in FIG. 13, particularly, could be formed with an upper portion similar to that illustrated in FIG. 7 actually embedded in the material in the general area of the slot 210.

While the embodiments of this invention shown and described are fully capable of achieving the objects and advantages desired, it is to be understood that such embodiments have been for purposes of illustration only and not for purposes of limitation.

We claim:

1. An orthopedic shoe comprising in combination: A rigid platform having an upper and lower surface wherein the said lower surface is essentially flat, but with an upwardly curved portion at its front and at its rear, and wherein the upper surface is so configured as to fit the lower surface of a human foot; at least one removable closure closing at least one opening adjacent the upper surface of said platform; at least one removably adhering flexible means building up a portion of the upper surface of said platform; foot encompassing strap means extending through a transverse opening in said platform; and means to fasten said foot encompassing strap about a human foot.

2. The apparatus of claim 1 wherein said foot encompassing strap is suitable to pass over a foot resting upon said platform and around the heel portion of said foot.

3. The apparatus of claim 2 wherein there are at least two closures closing at least two openings in said platform.

4. The apparatus of claim 3 wherein one of said openings is adjacent the toe portion of said platform and one is adjacent the heel portion of said platform.

5. The apparatus of claim 2 wherein the said upper surface slopes downward from that area which will be contacted by the ball of the foot to its front portion relative to a plane through the flat portion of the lower surface.

6. The apparatus of claim 5 wherein the said lower surface is covered over at least a portion thereof on its underside with a slip-proof material.

* * * * *